United States Patent [19]

Hicks

[11] Patent Number: 5,556,390
[45] Date of Patent: Sep. 17, 1996

[54] CATHETER WITH OVAL OR ELLIPTICAL LUMENS

[75] Inventor: Allen J. Hicks, Woodinville, Wash.

[73] Assignee: Quinton Instrument Company, Bothell, Wash.

[21] Appl. No.: 400,228

[22] Filed: Mar. 7, 1995

[51] Int. Cl.$^6$ ............................................. A61M 25/00
[52] U.S. Cl. ............................................. 604/280; 604/264
[58] Field of Search .................................. 604/39, 43, 93, 604/280, 40–42, 44, 45, 53, 264

[56] References Cited

U.S. PATENT DOCUMENTS

| | | | |
|---|---|---|---|
| Re. 31,873 | 4/1985 | Howes | 128/674 |
| 1,922,084 | 8/1933 | Gerow . | |
| 2,173,527 | 9/1939 | Agayoff . | |
| 2,175,726 | 10/1939 | Gebauer . | |
| 2,819,718 | 1/1958 | Goldman . | |
| 3,359,974 | 12/1967 | Khalil . | |
| 3,394,705 | 7/1968 | Abramson . | |
| 3,599,620 | 8/1971 | Balin . | |
| 3,726,281 | 4/1973 | Norton et al. . | |
| 3,746,003 | 7/1973 | Blake et al. . | |
| 3,799,172 | 3/1974 | Szpur . | |
| 3,828,767 | 8/1974 | Spiroff . | |
| 3,995,623 | 12/1976 | Blake et al. . | |
| 4,100,246 | 7/1978 | Frisch . | |
| 4,134,402 | 1/1979 | Mahurkar . | |
| 4,144,884 | 3/1979 | Tersteegen et al. . | |
| 4,168,703 | 9/1979 | Kenigsberg . | |
| 4,180,068 | 12/1979 | Jacobsen et al. . | |
| 4,202,332 | 5/1980 | Tersteegen et al. . | |
| 4,217,895 | 8/1980 | Sagae et al. . | |
| 4,257,416 | 3/1981 | Prager . | |
| 4,327,722 | 5/1982 | Groshong et al. . | |
| 4,385,631 | 5/1983 | Uthmann | 604/284 |
| 4,403,983 | 9/1983 | Edelman et al. | 604/43 |
| 4,406,656 | 9/1983 | Hattler et al. | 604/280 |
| 4,431,426 | 2/1984 | Groshong et al. | 604/280 |
| 4,451,252 | 5/1984 | Martin | 604/43 |
| 4,484,585 | 11/1984 | Baier | 128/748 |
| 4,493,696 | 1/1985 | Uldall | 604/43 |
| 4,543,087 | 9/1985 | Sommercorn et al. | 604/43 |
| 4,547,193 | 10/1985 | Rydell | 604/282 |
| 4,549,879 | 10/1985 | Groshong et al. | 604/247 |
| 4,559,046 | 12/1985 | Groshong et al. | 604/282 |
| 4,568,329 | 2/1986 | Mahurkar | 604/43 |
| 4,583,968 | 4/1986 | Mahurkar | 604/43 |
| 4,619,643 | 10/1986 | Bai | 604/43 |
| 4,623,327 | 11/1986 | Mahurkar | 604/4 |
| 4,642,092 | 2/1987 | Moss | 604/280 |
| 4,643,711 | 2/1987 | Bates | 604/43 |
| 4,682,978 | 7/1987 | Martin | 604/43 |
| 4,692,141 | 9/1987 | Mahurkar | 604/43 |
| 4,753,640 | 6/1988 | Nichols et al. | 604/247 |
| 4,756,303 | 7/1988 | Kawashima et al. | 128/6 |
| 4,772,268 | 9/1988 | Bates | 604/174 |
| 4,776,841 | 10/1988 | Catalano | 604/280 |
| 4,782,834 | 11/1988 | Maguire | 604/280 |
| 4,795,439 | 1/1989 | Guest | 604/280 |
| 4,808,155 | 2/1989 | Mahurkar | 604/43 |

(List continued on next page.)

FOREIGN PATENT DOCUMENTS

| | | |
|---|---|---|
| 1092927 | 1/1981 | Canada . |
| 1150122 | 7/1983 | Canada . |
| 0079719 | 5/1983 | European Pat. Off. . |
| 0333308 | 9/1989 | European Pat. Off. . |
| 1285953 | 7/1962 | France . |
| 2259865 | 6/1974 | Germany . |
| 8404043 | 10/1984 | WIPO . |

*Primary Examiner*—Randall L. Green
*Assistant Examiner*—Chalin Smith
*Attorney, Agent, or Firm*—Montgomery W. Smith; Richard D. Allison

[57] ABSTRACT

A single or multiple lumen catheter having one or more non-circular, oval, elliptical or oblong shaped lumens therein and wherein the cross sectional shapes of a plurality of the lumens in the multiple lumen catheters are opposed with respect to each other to minimize the existence of sharp corners or flow restriction areas in the lumen and minimizing the occurrence of septum or catheter wall deflection while maximizing the cross sectional area of the lumens of the catheter.

31 Claims, 5 Drawing Sheets

U.S. PATENT DOCUMENTS

| | | | |
|---|---|---|---|
| 4,822,345 | 4/1989 | Danforth | 604/282 |
| 4,838,881 | 6/1989 | Bennett | 604/280 |
| 4,894,057 | 1/1990 | Howes | 604/280 |
| 4,898,591 | 2/1990 | Jang et al. | 604/282 |
| 4,934,340 | 6/1990 | Ebling et al. | 128/6 |
| 4,961,809 | 10/1990 | Martin | 604/280 |
| 4,994,047 | 2/1991 | Walker | 604/280 |
| 4,995,865 | 2/1991 | Gahara et al. | 604/43 |
| 5,057,073 | 10/1991 | Martin | 604/43 |
| 5,106,368 | 4/1992 | Uldall et al. | 604/43 |
| 5,135,599 | 8/1992 | Martin et al. | 604/280 |
| 5,156,592 | 10/1992 | Martin et al. | 604/43 |
| 5,221,255 | 6/1993 | Mahurkar et al. | 604/43 |
| 5,221,256 | 6/1993 | Marhurkar | 604/280 |
| 5,348,536 | 9/1994 | Young et al. | 604/43 |
| 5,378,230 | 1/1995 | Mahurkar | 604/43 |
| 5,395,316 | 3/1995 | Martin | 604/280 |
| 5,425,714 | 6/1995 | Johnson | 604/280 |
| 5,437,637 | 5/1995 | Lieber | 604/280 |

CATHETER WITH OVAL OR ELLIPTICAL LUMENS

FIELD OF THE INVENTION

The present invention relates to single or multiple lumen catheters for use in medical applications including hemodialysis or other applications where access to the blood vessels of a patient is desired. More particularly, this invention relates to an improved catheter having one or more non-circular, oval, elliptical or oblong lumens including multiple lumen catheters wherein the cross sectional shapes of the lumens are opposed with respect to each other.

BACKGROUND OF THE INVENTION

Catheters have gradually evolved from single lumen catheters having a circular internal cross section to multiple lumen catheters which still use the circular cross section as the basic starting point for the shape of the outside of the catheter as well as the individual or combined shape of the multiple lumens. The use of the circular cross section lumen for a single lumen catheter provides the optimal flow characteristics because the frictional resistance to fluid flow through a circular lumen is minimized and there are no flow restrictive areas in the lumen. Additionally, laminar flow will occur through the lumen when a greater flow pressure is applied.

The designs for multiple lumen catheters have been created by splitting the circular cross section into multiple lumens. For example, one double lumen design which is used in the hemodialysis industry is the Circle-C lumen design. This cross sectional design involves reducing the cross sectional area of the main lumen and forming a second lumen concentrically along a portion of the outer surface thereof such that the overall shape of the catheter remains circular and the inner septum of the catheter looks basically like an eye brow. The most commonly used double lumen design in the hemodialysis industry is known as the Double-D lumen design. This design involves bisecting the circular cross section of a single lumen catheter to form two equal D-shaped lumens. Of these designs, only the Double-D design is believed to consistently provide flow rates for bi-directional blood flow of at least 250 ml per minute with a pressure gradient of less than 100 mm of mercury for a given outer diameter or French size.

The deficiencies inherent in the Circle-C designs are believed to be directly related to the existence of large flow restrictive and non laminar flow areas in the outer lumen due to the existence of sharp corners. Additionally, these designs include an increased amount of internal wall area which increases the amount of frictional resistance encountered by the fluid as it flows through the lumens of the catheter. The sharp corners of the Circle-C design create areas of lower or non laminar flow which increase the turbulence of fluid flow through the lumen as the velocity increases and may result in an increased likelihood that clots or other types of adhesions will form along the wall of the lumen in addition to the increased likelihood of hemolysis of the red blood cells occurring. To a lesser extent, the Double-D design has many of the same deficiencies present in the Circle-C design. For example, the Double-D design includes smaller flow restrictive areas than the Circle-C design although the flow of fluids through the lumens is still less than optimal due to the presence of lower or non laminar flow areas in the lumens adjacent to the intersection of the septum and the circular walls.

A further difficulty which arises with the Circle-C design and, to a lesser extent, with the Double-D design, is the deflection of the septum when the catheter is used for hemodialysis. In Hemodialysis, fluids are simultaneously infused and removed from the patient at high flow rates. With Double-D or Circle-C designs, fluid flows through one lumen in one direction and through the other lumen in the opposite direction. This bi-directional flow of fluids in the catheter is known to cause the deflection of the septum so that the flow area for fluid through one lumen is greater than in the other lumen and as one lumen becomes smaller than the other, the flow through the smaller lumen is further restricted for a given pressure.

Yet another difficulty which arises with the current Circle-C design and, to a lesser extent, with the Double-D design, is the reduction of flow when the catheter is bent or curved. When the catheters of these designs are bent or curved, the septum and, possibly the outer wall, of these catheters may deform to further restrict the flow of fluids through the lumens. One approach to solving the problem of septum deformation is disclosed in U.S. Pat. No. 5,221,255 granted to Mahurkar. In the Mahurkar patent, a separate rigid or semi-rigid member is disclosed to strengthen the septum of the catheter. In U.S. Pat. No. 5,348,538 granted to Young et al., the problem of septum deflection is addressed by coextruding the catheter with a plurality of materials having different durometers. In each of these designs, a significant and potentially expensive or time consuming modification of existing manufacturing methods and procedures may be required. In U.S. Pat. No. 5,156,592 granted to Martin et al., the concerns regarding septum deflection and wall collapse are addressed by the provision of a precurved catheter which is curved to conform to the shape of the incision typically formed in the body of the patient.

The present invention provides an optimal balance between the need to maximize the cross sectional area of the lumen of a catheter while minimizing the existence of sharp corners or flow restriction areas in the lumens. Similarly, the present invention provides an optimal balance between the need to minimize the occurrence of septum or wall deflection while providing a catheter with the smallest possible outer diameter for the intended use.

SUMMARY OF THE INVENTION

It is an object of the present invention to provide an improved catheter having one or more lumens therein which are oval, elliptical or oblong shaped.

It is a further object of the present invention to provide an improved catheter which has one or more lumens having a cross sectional shape to minimize the formation of clots or adhesions in the lumen due to the presence of restrictive or non laminar flow areas in the lumen.

It is a further object of the present invention to provide an improved catheter which has one or more lumens having a cross sectional shape to minimize the occurrence of hemolysis due to the presence of restrictive or non laminar flow areas in the lumen.

It is a further object of the present invention to provide an improved catheter having multiple lumens wherein the thickness and strength of the septum and outer walls of the catheter are maximized.

In one form of the present invention, the catheter is a single lumen catheter with a lumen having a generally egg, elliptical, oval or oblong shaped cross section formed by a pair of acute semicircular ends. The variable wall thickness of the catheter strengthens the outer walls of a circular catheter thereby minimizing the likelihood that the catheter will kink when it is bent or curved. The outer cross sectional shape of this form of the catheter may assume a variety of desired shapes including circular, elliptical, oval or oblong.

In another form of the present invention, the catheter is a dual lumen catheter having a pair of generally egg, or elliptical shaped lumens. In this embodiment, the lumens are preferably oppositely oriented to maximize the fluid flow area of each lumen in the catheter while not providing any or at least minimizing the areas of reduced or non laminar fluid flow in the catheter. As with the prior form of the present invention the lumens are generally formed by a pair of acute semicircular ends and include a septum having an area of increased thickness to minimize septum deflection during use with high velocity fluids.

In another form of the present invention, the catheter includes three or more lumens. In this embodiment, at least two of the lumens are generally egg, oblong or elliptical shaped and the remaining lumens may be of nearly any desired shape so that a guide wire or other instrument may be inserted therein or a medication or other fluid may be injected therethrough or withdrawn therefrom. As with the embodiments described above, the septum of the catheter includes an area of increased thickness and the outer wall of the catheter may also include one or more areas of increased thickness to resist deflection as the catheter is bent or used with high velocity fluids.

An advantage of the present invention is that the internal shape of the lumen provides for the smooth laminar flow of fluids therethrough with no significant flow restrictive areas so that the turbulence of the flow of fluid therethrough is minimized thereby reducing the likelihood that clots or adhesions will form in the lumen and minimizing the occurrence of hemolysis.

A further advantage of the present invention is that the septum which separates and/or surrounds the lumens of the catheter strengthens the catheter to minimize the effects of bending or curving the catheter upon insertion while being resistant to septum deflection when fluids are individually or simultaneously infused and withdrawn through the lumens at rapid rates or flows.

Yet another advantage of the present invention is that the outer shape of the catheter may be circular, elliptical, oblong, oval or otherwise shaped without affecting the function or operation of the catheter.

DESCRIPTION OF THE PREFERRED EMBODIMENTS

Figure 1:
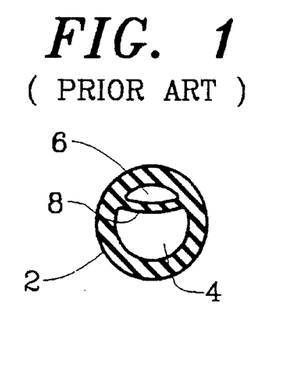
FIG. 1 is a cross sectional view of a prior art catheter showing the Circle-C cross sectional shape of a double lumen catheter.
Figure 2:
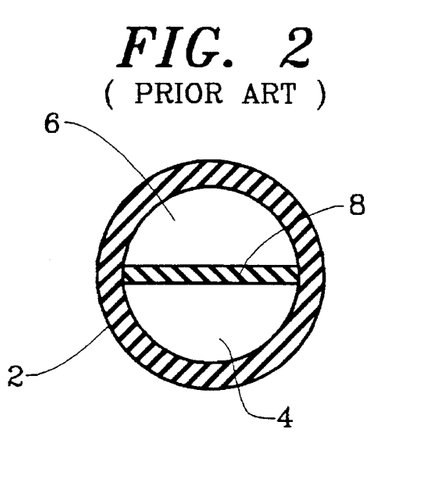
FIG. 2 is a cross sectional view of a prior art catheter showing the Double-D cross sectional shape of a double lumen catheter.

FIGS. 1 and 2 represent the cross sectional views of two prior art dual lumen catheters 2. These catheters 2 include first and second lumens, 4 and 6 respectively, and a generally uniform thickness septum 8 which extends between the respective lumens. As shown in the drawings, the outer wall 9 of the prior art catheters 2 is also generally uniform in thickness.

As shown in FIGS. 3–10, the preferred catheter assemblies 10 generally include an elongate body portion 12 having a generally circular cross section. The body portion 12 may include a tip member 14 on the distal end portion thereof and a Y-shaped connector hub 16 on the proximal end portion thereof. The proximal end portion of the connector hub 16 includes one or more extension members 18 thereon.

As used herein, the term "proximal" is intended to refer to the end or portion of a member or element which is normally oriented or positioned away from the patient in use while the term "distal" is intended to refer to the end or portion of a member or element which is nearest to the patient in use. Although the most preferred form and use of the present invention is a dual lumen catheter for use in hemodialysis, the present invention may include one or more lumens therein and may be used for central venous access, infusion or other types of access to the blood vessels or treatment of the patient.

Figure 3:
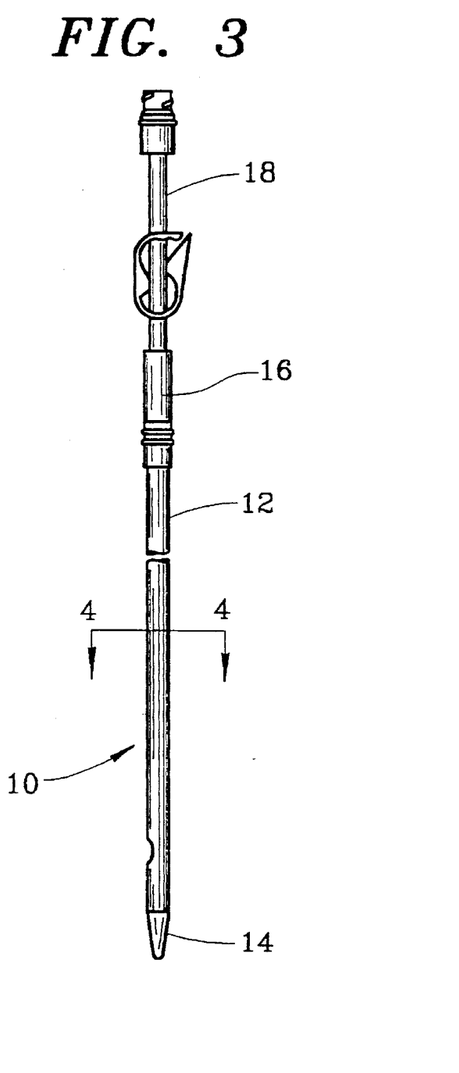
FIG. 3 is an elevated side view of a single lumen catheter in accordance with the present invention.
Figure 4:
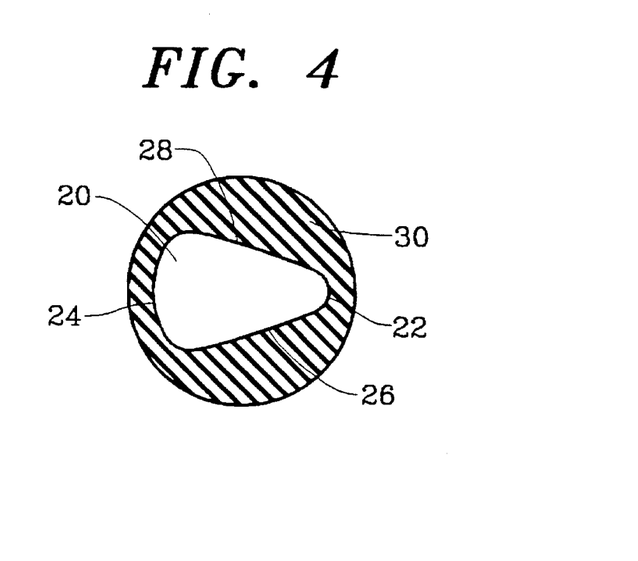
FIG. 4 is a cross sectional view of the catheter of FIG. 3 taken generally along lines 4—4 of FIG. 3.
Figure 13:
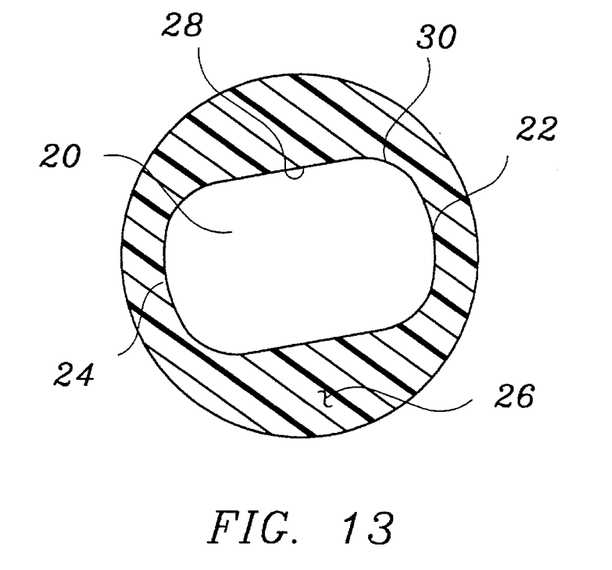
FIG. 13 is a cross sectional view of a further embodiment of the catheter of the present invention.

FIGS. 3 and 4 are illustrative of a single lumen catheter formed in accordance with the present invention. The single lumen catheter includes a body portion 12 with a tip member 14 at the distal end thereof and a hub 16 and extension member on the proximal end thereof. As shown in FIG. 4, the lumen 20 of this embodiment is generally egg or elliptical shaped. The lumen is formed by a first curved end 22 and a second curved end 24. In this embodiment, the radius of the first curved end 22 may be less than or equal the radius of the second curved end 24 and the first side 26 and second side 28 of the lumen are formed by generally straight surfaces to interconnect the first and second curved ends to form the referred ovoid shape of the lumen 20. Because the desired cross sectional shape of this embodiment is circular, the outer wall 30 is thicker adjacent to the first curved end 22 than the second curved end 24 and the thickness of the outer wall 30 decreases along the length of the first and second sides from the first curved end 22 and the second curved end 24. If the radius of the first curved end 22 were equal to the radius of the second curved end 24, the cross sectional shape of the lumen 20 would be oblong (See FIG. 13) and the thickness of the outer wall could be varied to form areas of increased thickness as described above.

Figure 5:
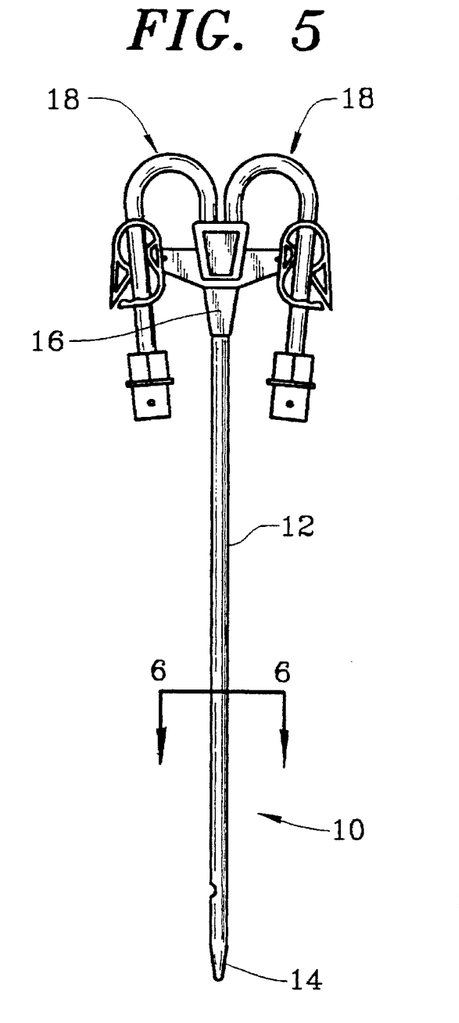
FIG. 5 is an elevated side view of a double lumen catheter in accordance with the present invention.
Figure 6:
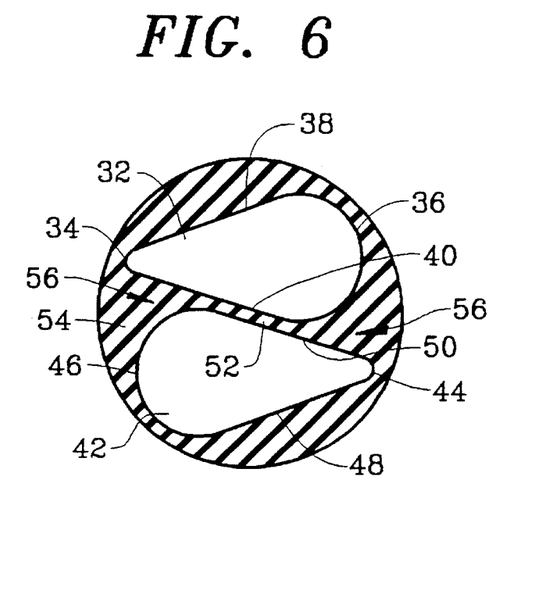
FIG. 6 is a cross sectional view of the catheter of FIG. 5 taken generally along lines 6—6 of FIG. 5.
Figure 7:
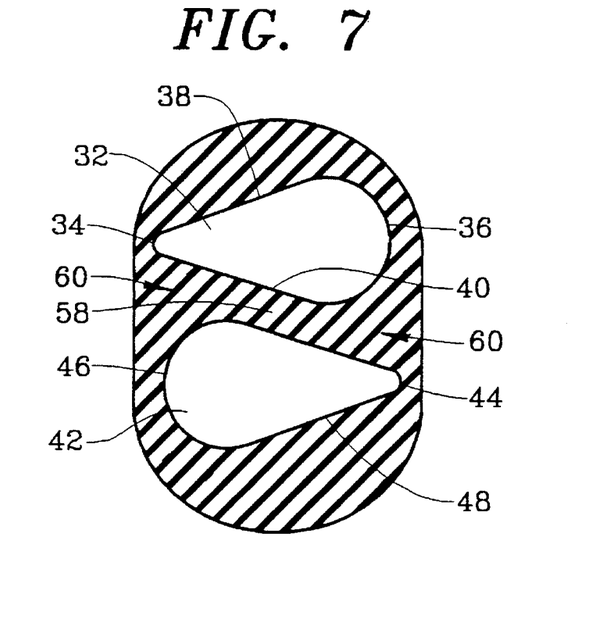
FIG. 7 is a cross sectional view of an alternate embodiment of a double lumen catheter having a generally oblong cross sectional configuration.

FIGS. 5, 6 and 7 are illustrative of a dual lumen catheter formed in accordance with the present invention. The dual lumen catheter includes a body portion 12 with a tip member 14 at the distal end thereof. The proximal end of this embodiment includes a hub member 16 and a pair of extension members 18 thereon. As shown in FIG. 6, the preferred form of this embodiment includes a pair of generally egg or elliptically shaped lumens. The first lumen 32 is formed by a first curved end 34 and a second curved end 36. In this embodiment, the radius of the first curved end 34 is generally less than the radius of the second curved end 36 and preferably less than about one-half of the radius of the second curved end 36. The first side 38 and second side 40 of the first lumen 32 are formed by generally straight surfaces which interconnect the first and second curved ends to form the preferred ovoid shape of the lumen 32. The second lumen 42 is formed by a first curved end 44 and a second curved end 46. As with the first lumen 32, the radius of the first curved end 44 of the second lumen 42 is generally less than the radius of the second curved end 46 and preferably less than about one-half of the radius of the second curved end 46. The first side 48 and second side 50 of the second lumen 42 are formed by generally straight surfaces which interconnect the first and second curved ends to form the preferred ovoid shape of the second lumen 42.

As shown in FIG. 6, the first and second lumens are 180 degrees opposed in orientation with respect to each other to form a septum 52 therebetween. The septum 52 is formed by the second side 40 of the first lumen 32 and the second side 50 of the second lumen 42 and may be formed to vary in thickness between the lumens (FIGS. 6 and 7) to minimize deflection of the septum 52 during use of the catheter. The preferred shape of the septum 52 generally resembles a slightly deformed I-beam shape such that the ends of the septum 52 are thicker and stronger than the middle portion thereof.

As with the prior embodiment, the outer wall 54 of the present embodiment preferably varies in thickness to minimize the likelihood that the catheter will kink when bent, curved or under internal pressure. The thickness of the outer wall increases along the second side 40 and 50 of the first and second lumens, 32 and 42, respectively from second curved ends, 36 and 46, to the first curved ends, 34 and 44, of the respective lumens. Additionally, the portion of the outer wall adjacent to the ends of the septum 52 form an even thicker and generally diamond shaped area 56 which further reinforces the catheters to minimize deflection of the septum 52 and kinking of the catheter during use.

FIG. 7 is illustrative of a further embodiment of the present invention wherein the cross sectional shape of the catheter is generally oblong. The dual lumen catheter of this embodiment includes a body portion with a tip member at the distal end thereof as described above. The proximal end of this embodiment may also include a hub member and a pair of extension members thereon. As with the embodiment shown in FIGS. 5 and 6, this embodiment preferably includes a pair of generally egg or elliptical shaped lumens although, oblong lumens (not shown) may also be used with the embodiment shown in FIGS. 5 and 6 or 7. The first lumen 32 of this embodiment is formed by a first curved end 34 and a second curved end 36. In this embodiment, the radius of the first curved end 34 is generally less than and preferably less than approximately one-half the radius of the second curved end 36. The first side 38 and second side 40 of the first lumen 32 are formed by generally straight surfaces which interconnect the first and second curved ends to form the preferred ovoid shape of the lumen 32.

The second lumen 42 of the embodiment shown in FIG. 7 is formed by a first curved end 44 and a second curved end 46. As with the first lumen 32, the radius of the first curved end 44 of the second lumen 42 is generally less than the radius of the second curved end 46 and preferably less than approximately one-half of the radius of the second curved end 46. The first side 48 and second side 50 of the second lumen 42 are formed by generally straight surfaces which interconnect the first and second curved ends to form the preferred ovoid shape of the second lumen 42. As with the embodiment shown in FIGS. 5 and 6, the first and second lumens of the embodiment shown in FIG. 7 are 180 degrees opposed in orientation with respect to each other to form a septum 52 therebetween. The septum 52 of this embodiment is formed by the second side 40 of the first lumen 32 and the second side 50 of the second lumen 42 and may be formed to be generally uniform in thickness between the lumens. The outer wall 54 of the present embodiment preferably varies in thickness to minimize the likelihood that the catheter will kink when bent, curved or under pressure in use. The thickness of the outer wall increases along the second side 40 and 50 of the first and second lumens, 32 and 42, respectively from second curved ends, 36 and 46, to the first curved ends, 34 and 44, of the respective lumens. Additionally, the portion of the outer wall adjacent to the ends of the septum 58 form an even thicker and generally diamond shaped area 60 which further reinforces the septum 58 of the catheter to minimize deflection of the septum 58 and kinking of the catheter.

Figure 8:
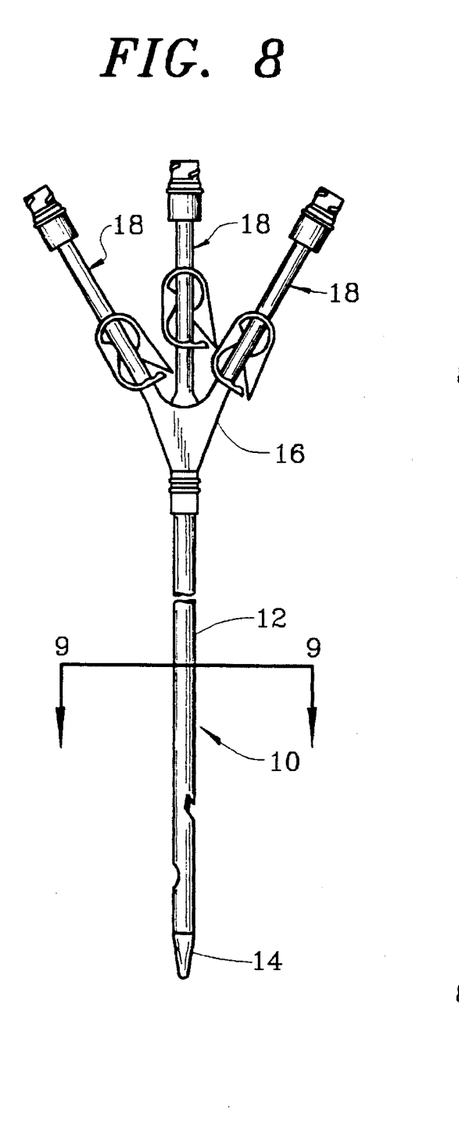
FIG. 8 is an elevated side view of a triple lumen catheter in accordance with the present invention.
Figure 9:
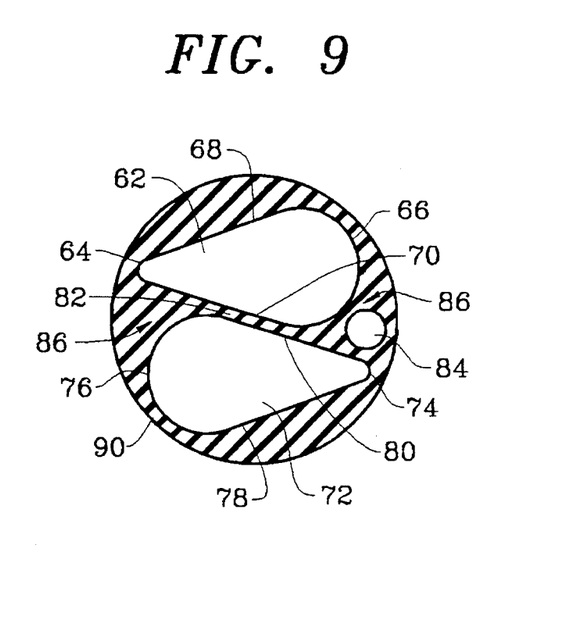
FIG. 9 is a cross sectional view of the catheter of FIG. 8 taken generally along lines 9—9 of FIG. 8.

FIGS. 8–12 are illustrative of further multi-lumen catheters formed in accordance with the present invention. The multi-lumen catheters include a body portion with a tip member at the distal end thereof. The proximal end of these embodiments may include a hub member and a pair of extension members thereon. As shown in FIGS. 8 and 9, this embodiment includes at least a pair of generally egg or elliptical shaped lumens. The first lumen 62 is formed by a first curved end 64 and a second curved end 66. In this embodiment, the radius of the first curved end 64 is generally less than the radius of the second curved end 66 and more preferably less than approximately one-half of the radius of the second curved end 66. The first side 68 and second side 70 of the first lumen 62 are formed by generally straight surfaces which interconnect the first and second curved ends to form the preferred ovoid shape of the lumen 62.

Figure 10:
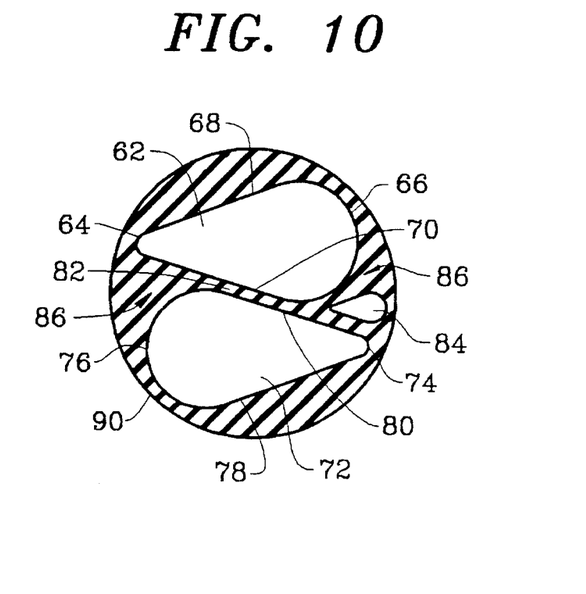
FIG. 10 is a cross sectional view of an alternate embodiment of a triple lumen catheter having three generally ovoid lumens.

As shown in FIG. 9, the second lumen 72 is formed by a first curved end 74 and a second curved end 76. As with the first lumen 62 of this embodiment, the radius of the first curved end 74 of the second lumen 72 is generally less than the radius of the second curved end 76 and more preferably less than approximately one-half of the radius of the second curved end 76. The first side 78 and second side 80 of the second lumen 72 are formed by generally straight surfaces which interconnect the first and second curved ends to form the preferred ovoid shape of the second lumen 72. As best shown in FIG. 9, the first and second lumens are preferably 180 degrees opposed in orientation with respect to each other to form a septum 82 therebetween. The septum 82 is formed by the second side 70 of the first lumen 62 and the second side 80 of the second lumen 72 and may be formed to vary in thickness between the lumens as shown in FIGS. 9 and 10 to minimize the potential deflection of the septum 82 during use of the catheter. As with the prior embodiments, the septum 82 preferably has a generally I-beam type of shape wherein the ends of the septum 82 are formed by the generally diamond shaped areas 86 which are thicker than the middle portion of the septum 82 to minimize the deflection thereof. Additionally, the portion of the septum 82 adjacent to the outer wall 90 is preferably the thickest part of the catheter so that the likelihood of bending or kinking is minimized during use.

The present embodiment also includes a third lumen 84 which extends between the distal and proximal end portions of the catheter. As shown in FIG. 9, the third lumen 84 preferably has a circular cross section although it may also be formed to include an ovoid shape as shown in FIG. 10. The third lumen 84 is typically used to infuse medications or withdraw blood samples from the patient although the third lumen 84 may also by used for a guide wire or stiffener during insertion or use of the catheter. As shown in FIGS. 9 and 10, the third lumen 84 is preferably located in one of the generally diamond shaped areas 86 which form part of the septum 82 and outer wall 88 of the catheter. The third lumen 84 is preferably sized and positioned in the diamond shaped area 86 such that the strength of the outer wall 88 of the catheter is not compromised or reduced so that the likelihood of kinking or septum deflection is not significantly increased even with the third lumen 84 present in the catheter.

As with the prior embodiments, the outer wall 90 of the present embodiment preferably varies in thickness to minimize the likelihood that the catheter will kink when bent, curved or under pressure during use. The thickness of the outer wall 90 increases along the second side 70 and 80 of the first and second lumens, 62 and 72, respectively from second curved ends, 66 and 76, to the first curved ends, 64 and 74, of the respective lumens. Additionally, the portion of the outer wall adjacent to the ends of the septum 82 form the thicker and generally diamond shaped areas 86 to further reinforce the lumens and cross sectional integrity of the catheter to minimize deflection of the septum 82 in use and inhibit the kinking or bending of the catheter.

Figure 11:
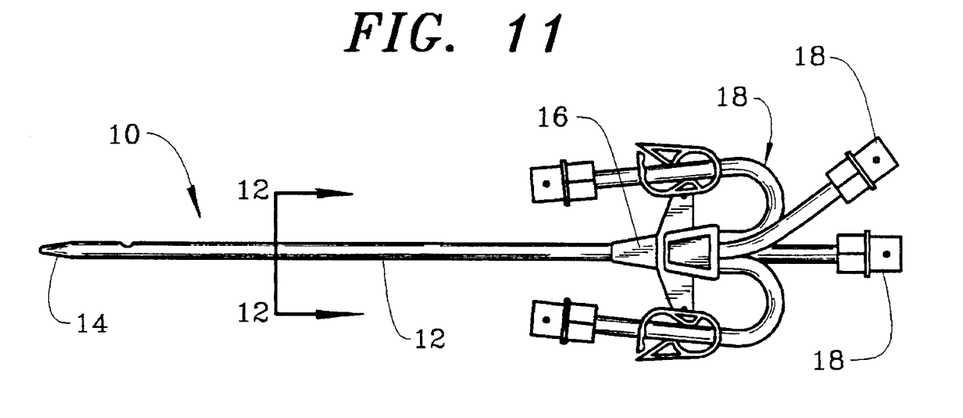
FIG. 11 is an elevated side view of a catheter having four lumens therein in accordance with the present invention.
Figure 12:
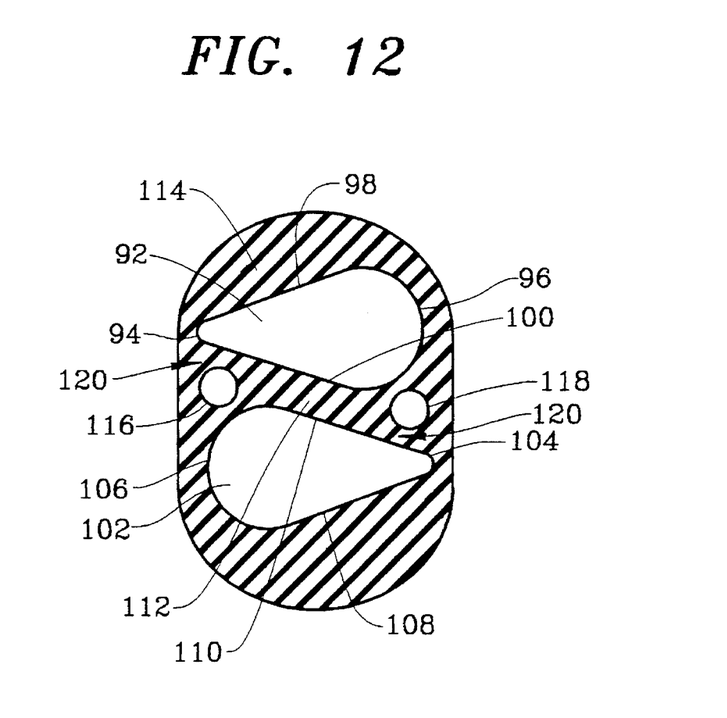
FIG. 12 is a cross sectional view of the catheter of FIG. 11 taken generally along lines 12—12 of FIG. 11.

FIGS. 11 and 12 are illustrative of a further embodiment of the present invention wherein the cross sectional shape of the catheter is generally oblong. The multi-lumen catheter of this embodiment includes a body portion with a tip member at the distal end thereof as described above. The proximal end of this embodiment includes also includes a hub member and a pair of extension members thereon. As with the embodiment shown in FIGS. 9 and 10, this embodiment includes a plurality of generally egg or elliptical shaped lumens. The first lumen 92 is formed by a first curved end 94 and a second curved end 96. In this embodiment, the radius of the first curved end 94 is less than approximately one-half the radius of the second curved end 96. The first side 98 and second side 100 of the first lumen 92 are formed by generally straight surfaces which interconnect the first and second curved ends to form the preferred ovoid shape of the lumen 92. The second lumen 102 is formed by a first curved end 104 and a second curved end 106. As with the first lumen 92, the radius of the first curved end 104 of the second lumen 102 is less than the radius of the second curved end 106. The first side 108 and second side 110 of the second lumen 102 are formed by generally straight surfaces which interconnect the first and second curved ends to form the preferred ovoid shape of the second lumen 102. As with the embodiment shown in FIG. 7, the first and second lumens of the embodiment shown in FIG. 12 are preferably about 180 degrees opposed in orientation with respect to each other to form a septum 112 therebetween. The septum 112 is formed by the second side 98 of the first lumen 92 and the second side 110 of the second lumen 102 and may be formed to be generally uniform in thickness between the lumens. The third and fourth lumens, 116 and 118, of this embodiment preferably have a circular cross sectional shape for the receipt of a stiffener or guidewire in one of the lumens and to allow for the infusion of medications and/or the withdrawal of blood samples through the other of the lumens.

As with the prior embodiment, the outer wall 114 of the present embodiment preferably varies in thickness to minimize the likelihood that the catheter will kink when bent, curved or under pressure in use. The thickness of the outer wall 114 in this embodiment may be generally uniform or gradually increasing along the second side 100 and 110 of the first and second lumens, 92 and 102, respectively from second curved ends, 96 and 106, to the first curved ends, 94 and 104, of the respective lumens. Additionally, the portion of the outer wall adjacent to the ends of the septum 112 form an even thicker and pair of generally diamond shaped areas 120 which further reinforce the septum 112 of the catheter to minimize deflection of the septum 112 and kinking of the catheter during insertion or use.

Figure 14:
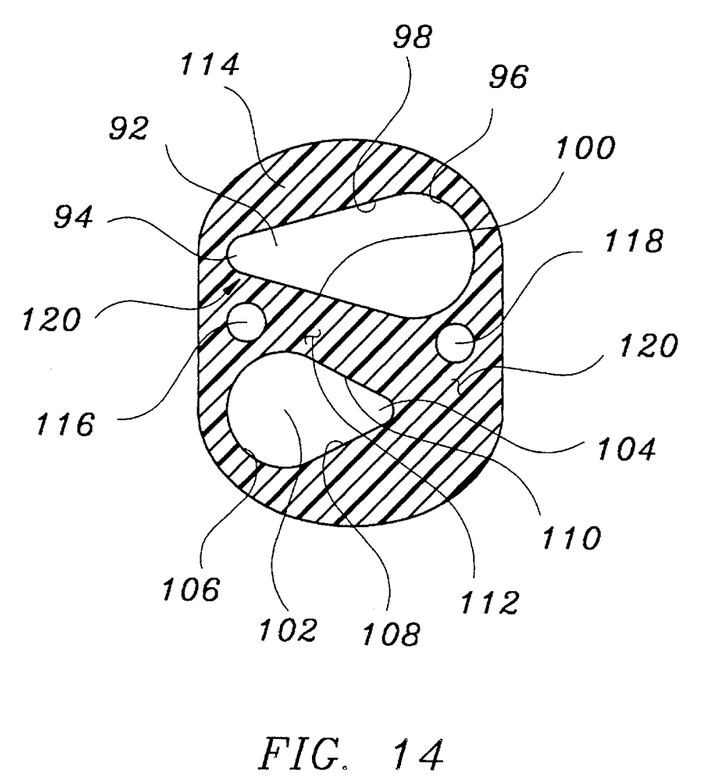
FIG. 14 is a cross sectional view of a further embodiment of the catheter of the present invention.

In addition to the generally non linear septum of the prior art catheter shown in FIG. 1, FIG. 14 illustrates an embodiment of the present invention having a generally non linear septum where like numbers have been added like members of the embodiment described above and shown in FIGS. 11 and 12.

What is claimed is:

1. A dual lumen catheter for use in the body of the patient comprising;

an elongated and generally cylindrical body portion having distal and proximal end portions and a pair of opposingly oriented lumens extending therebetween wherein the cross sectional area of said catheter includes each of said lumens formed of a first curved end with a first acute radius of curvature and a second curved end with a second acute radius of curvature and said first radius of curvature is greater than said second radius of curvature and said first and second curved ends face each other and further include generally elongate side portions therebetween.

2. The catheter of claim 1 wherein said side portions of said lumen are generally linear between said first radius of curvature and said second radius of curvature.

3. The catheter of claim 1 wherein said first radius of curvature of said first curved end is approximately less than one-half of said second radius of curvature of said second curved end.

4. The catheter of claim 1 wherein said side portions are generally parallel to each other.

5. The catheter of claim 1 wherein said body portion includes a plurality lumens extending through at least a portion thereof.

6. The catheter of claim 5 wherein said first thickness is greater than said second thickness.

7. The catheter of claim 1 wherein said body portion includes a plurality of lumens therein and at least two of said lumens have different cross sectional shapes.

8. The catheter of claim 5 wherein said lumens are opposingly oriented to each other.

9. The catheter of claim 8 wherein said first radius of curvature of said first lumen is generally adjacent to said second radius of curvature of said second lumen.

10. The catheter of claim 9 wherein said first radius of curvature of said first lumen is generally adjacent to a second radius of curvature of a second lumen.

11. The catheter of claim 8 wherein said plurality of lumens are separated by a septum having a generally constant thickness.

12. The catheter of claim 1 wherein said body portion includes a plurality of lumens therein and the cross sectional shape of said lumens are substantially similar.

13. The catheter of claim 12 wherein the cross sectional shapes of said lumens are opposingly oriented.

14. A catheter for use in the body of the patient comprising;

an elongated and generally cylindrical body portion having distal and proximal end portions and at least one lumen extending therebetween wherein the cross sectional area of said catheter includes at least one lumen formed by a first curved end with a first acute radius of curvature and a second curved end with a second acute radius of curvature and further includes generally elongate side portions therebetween and wherein said first radius of curvature of said first curved end faces said second radius of curvature of said second curved end and said second radius of curvature of said second curved end faces said first radius of curvature of said first curved end and said first radius of curvature of said first curved end is generally less than approximately one-half of said second radius of curvature of said second curved end.

15. The catheter of claim 14 wherein said side portions of said lumen are generally linear between said first radius of curvature and said second radius of curvature.

16. The catheter of claim 14 wherein said body portion includes a plurality of lumens extending through at least a portion thereof.

17. The catheter of claim 16 wherein said lumens are separated by a septum having nonlinear sides.

18. The catheter of claim 16 wherein said lumens are opposingly oriented to each other.

19. The catheter of claim 18 wherein said first radius of curvature of said first lumen is generally adjacent to a second radius of curvature of a second lumen.

20. A catheter for use in the body of the patient comprising;

an elongated and generally cylindrical body portion having distal and proximal end portions and at least one lumen extending therebetween wherein the cross sectional area of said at least one lumen of said catheter is ovoid shaped and is formed by a first curved end with a first acute radius of curvature and a second curved end with a second acute radius of curvature wherein said first and second curved ends face each other and said first acute radius is less than said second acute radius and further include generally elongate side portions therebetween.

21. The catheter of claim 20 wherein said side portions of said lumen are generally linear between said first radius of curvature and said second radius of curvature.

22. The catheter of claim 20 wherein said body portion includes a plurality of lumens extending through at least a portion thereof and said lumens are separated by a septum.

23. The catheter of claim 22 wherein said plurality of lumens are opposingly oriented with respect to each other along opposite sides of said septum.

24. The catheter of claim 22 wherein said septum includes a first thickness adjacent said first radius of curvature and a second thickness adjacent said second radius of curvature wherein said first thickness is greater than said second thickness.

25. A catheter for use in the body of the patient comprising;

an elongated and generally cylindrical body portion having distal and proximal end portions and at least one lumen extending therebetween wherein the cross sectional area of said catheter includes at least one lumen formed of a first curved end with a first acute radius of curvature and a second curved end with a second acute radius of curvature wherein said second radius of curvature is less than said first radius of curvature and said first radius of curvature faces said second radius of curvature and said second radius of curvature faces said first radius of curvature and said lumen further includes a pair of generally elongate side portions extending between said first and second curved ends wherein said side portions face each other.

26. The catheter of claim 25 wherein said side portions of said lumen are generally linear between said first radius of curvature and said second radius of curvature.

27. The catheter of claim 25 wherein said body portion includes a plurality of lumens extending through at least a portion thereof and said lumens are separated by a septum.

28. The catheter of claim 27 wherein said plurality of lumens are opposingly oriented with respect to each other along opposite sides of said septum.

29. The catheter of claim 27 wherein said septum includes a first thickness adjacent said first radius of curvature and a second thickness adjacent said second radius of curvature wherein said first thickness is greater than said second thickness.

30. A dual lumen catheter for use in the body of the patient comprising;

an elongated and generally cylindrical body portion having distal and proximal end portions and a pair of opposingly oriented lumens extending therebetween wherein the cross sectional area of each of said lumens of said catheter is ovoid shaped and is formed by a first curved end with a first acute radius of curvature and a second curved end with a second acute radius of curvature wherein said first and second curved ends face each other and further include generally elongate side portions therebetween.

31. A dual lumen catheter for use in the body of the patient comprising;

an elongated and generally cylindrical body portion having distal and proximal end portions and a pair of opposingly oriented lumens extending therebetween wherein the cross sectional area of said catheter includes said lumens being formed of a first curved end with a first acute radius of curvature and a second curved end with a second acute radius of curvature wherein said second radius of curvature is less than said first radius of curvature and said first radius of curvature faces said second radius of curvature and said second radius of curvature faces said first radius of curvature and said lumen further includes a pair of generally elongate side portions extending between said first and second curved ends wherein said side portions face each other.

* * * * *